US00PP34495P2

(12) United States Plant Patent
Whitehead

(10) Patent No.: US PP34,495 P2
(45) Date of Patent: Aug. 16, 2022

(54) ***QUERCUS* TREE NAMED 'QVCCN'**

(50) Latin Name: *Quercus virginiana*
Varietal Denomination: QVCCN

(71) Applicant: Dan Milton Whitehead, Lincolnton, GA (US)

(72) Inventor: Dan Milton Whitehead, Lincolnton, GA (US)

(73) Assignee: Dan Milton Whitehead, Lincolnton, GA (US)

( * ) Notice: Subject to any disclaimer, the term of this patent is extended or adjusted under 35 U.S.C. 154(b) by 0 days.

(21) Appl. No.: 17/582,235

(22) Filed: Jan. 24, 2022

(51) Int. Cl.
*A01H 5/00* (2018.01)
*A01H 6/00* (2018.01)

(52) U.S. Cl.
USPC ..... Plt./225

(58) Field of Classification Search
USPC ..... Plt./225
See application file for complete search history.

*Primary Examiner* — Susan McCormick Ewoldt
(74) *Attorney, Agent, or Firm* — Penny J. Aguirre

(57) ABSTRACT

A new cultivar of *Quercus virginiana* tree named 'QVCCN' that is characterized by its resilience to cold winter weather in South Carolina with a canopy that retains its previous years foliage rather than defoliating (appearing evergreen), its compact and dense canopy, its foliage that is dark green in color, and its upright branching habit.

3 Drawing Sheets

Botanical classification: *Quercus virginiana.*
Variety denomination: 'QVCCN'.

BACKGROUND OF THE INVENTION

The present invention relates to a new and distinct cultivar of *Quercus virginiana* and will be referred to hereafter by its cultivar name, 'QVCCN'. 'QVCCN' is a new live oak tree grown for use as a landscape plant.

'QVCCN' was discovered by the Inventor as a chance seedling that was growing in a field plot of over 200 unnamed and unpatented plants of *Quercus virginiana* in Iva, S.C. in November of 2017. The exact parentage is therefore unknown.

Asexual propagation of the new cultivar was first accomplished under the direction of the Inventor using stem cuttings in November of 2018 in Eatonton, Ga. Asexual propagation by stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'QVCCN' as a unique cultivar of *Quercus.*

1. 'QVCCN' exhibits resilience to cold winter weather in South Carolina with a canopy that retains its previous years foliage rather than defoliating (appearing evergreen).
2. 'QVCCN' exhibits a compact and dense canopy.
3. 'QVCCN' exhibits foliage that is dark green in color.
4. 'QVCCN' exhibits an upright branching habit.
5. 'QVCCN' exhibits an upright-oval form.

Plants of the species *Quercus virginiana* that were growing in the plot where the claimed plant was discovered, all differ from 'QVCCN' in having lighter colored foliage that defoliates in cold weather, less upright branch angles, and a less dense and less compact plant habit. 'QVCCN' can be most closely compared to the *Quercus virginiana* cultivars 'SDLN' (U.S. Plant Pat. No. 12,015) and 'FBQV22' (U.S. Plant Pat. No. 19,758). 'SDLN' and 'FBQV22' are both similar to 'QVCCN' in having a dense canopy and foliage that is dark green in color. 'SDLN' differs from 'QVCCN' in having wider branch angles, a broader plant habit, and in not retianing a heavy foliage canopy in winter in the Piedmont region of South Carolina. 'FBQV22' differs from 'QVCCN' in having wider branch angles, a broader plant form, leaves that are more narrow, and in not retianing a heavy foliage canopy in winter.

BRIEF DESCRIPTION OF THE DRAWINGS

The accompanying colored photographs illustrate the overall appearance and distinct characteristics of the new cultvar of *Quercus*. The plant in the photographs in FIG. 1 and FIG. 2 were taken of a tree about 13 years in age as grown in a garden in Iva, S.C.

The photograph in FIG. 1 provides a side view of the plant habit of 'QVCCN'.

Figure 1:
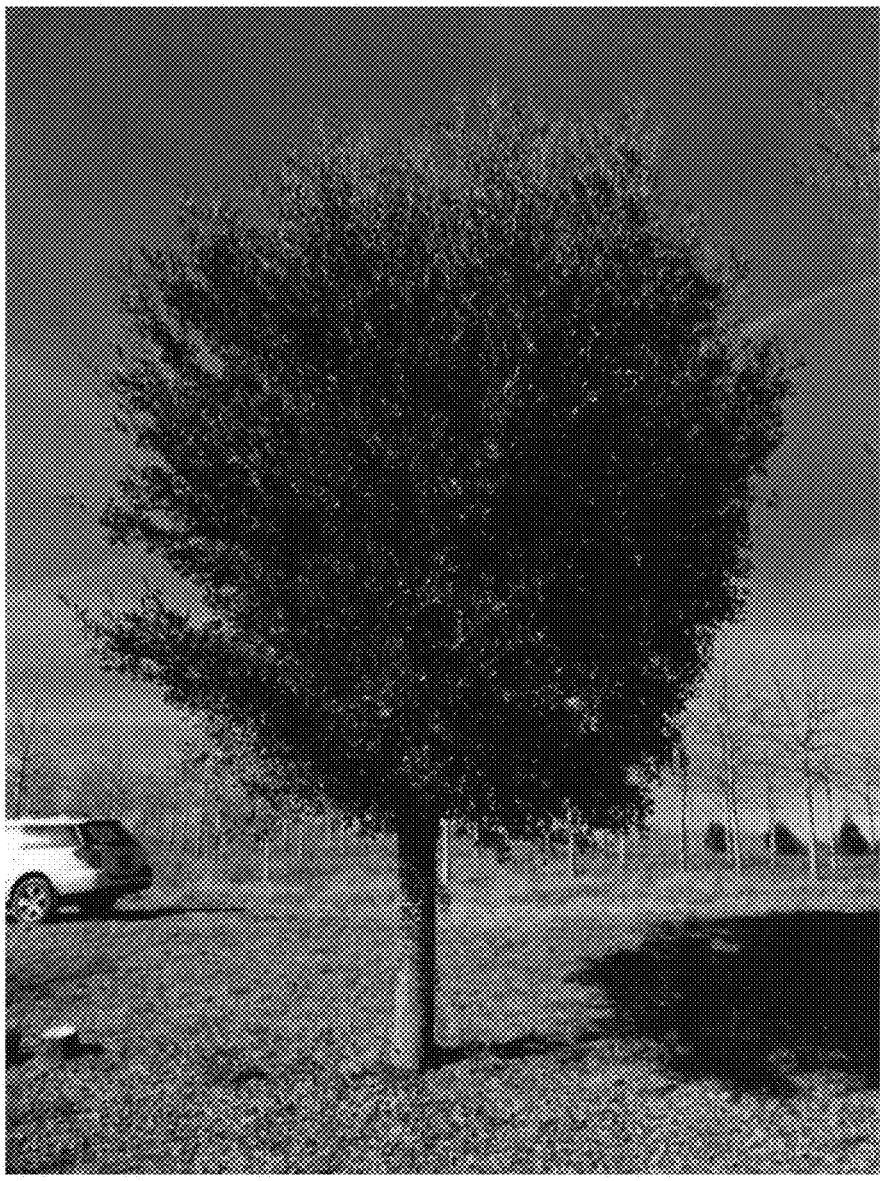
Figure 2:
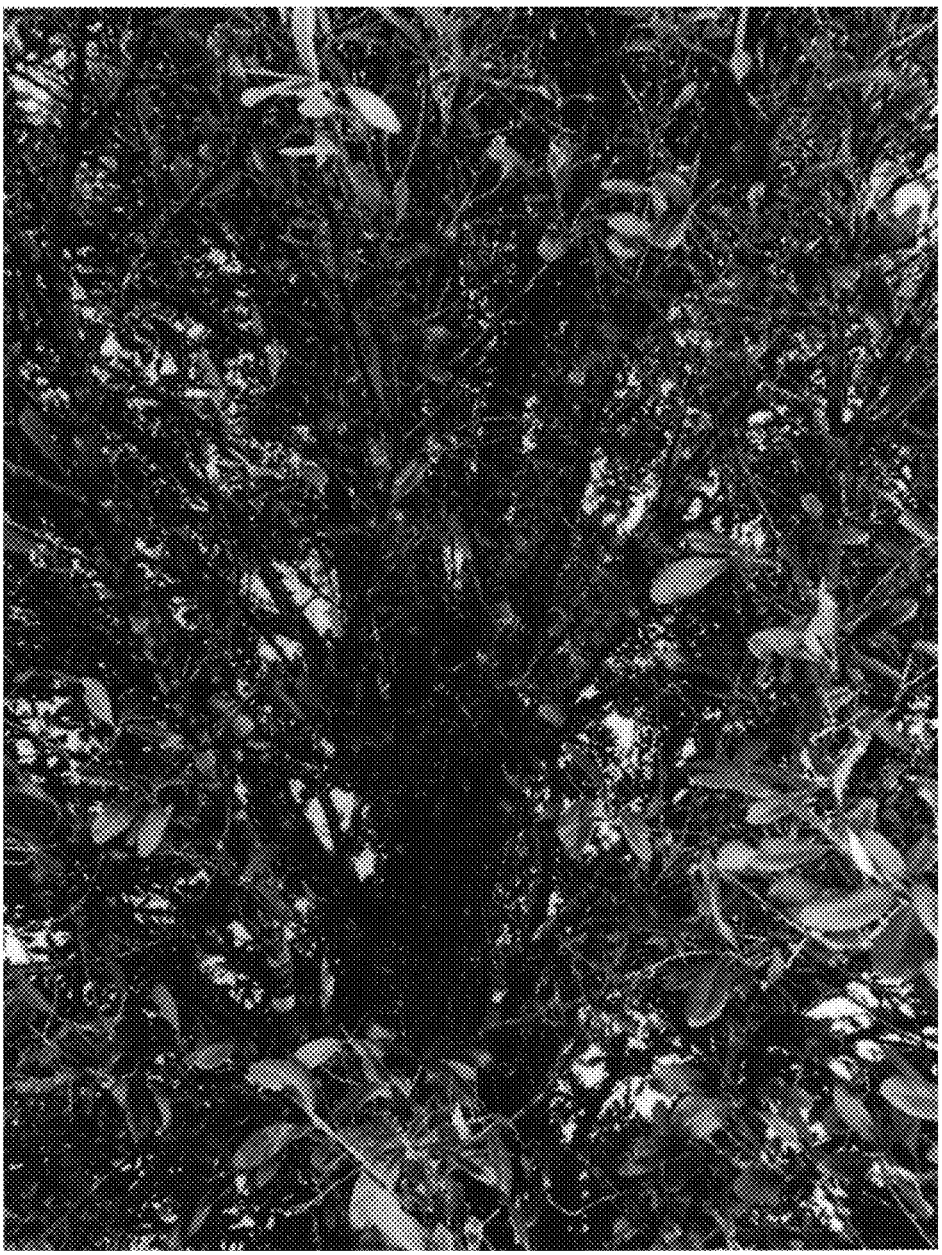

The photograph in FIG. 2 provides a close-up view of the branch angles of 'QVCCN'.

Figure 3:
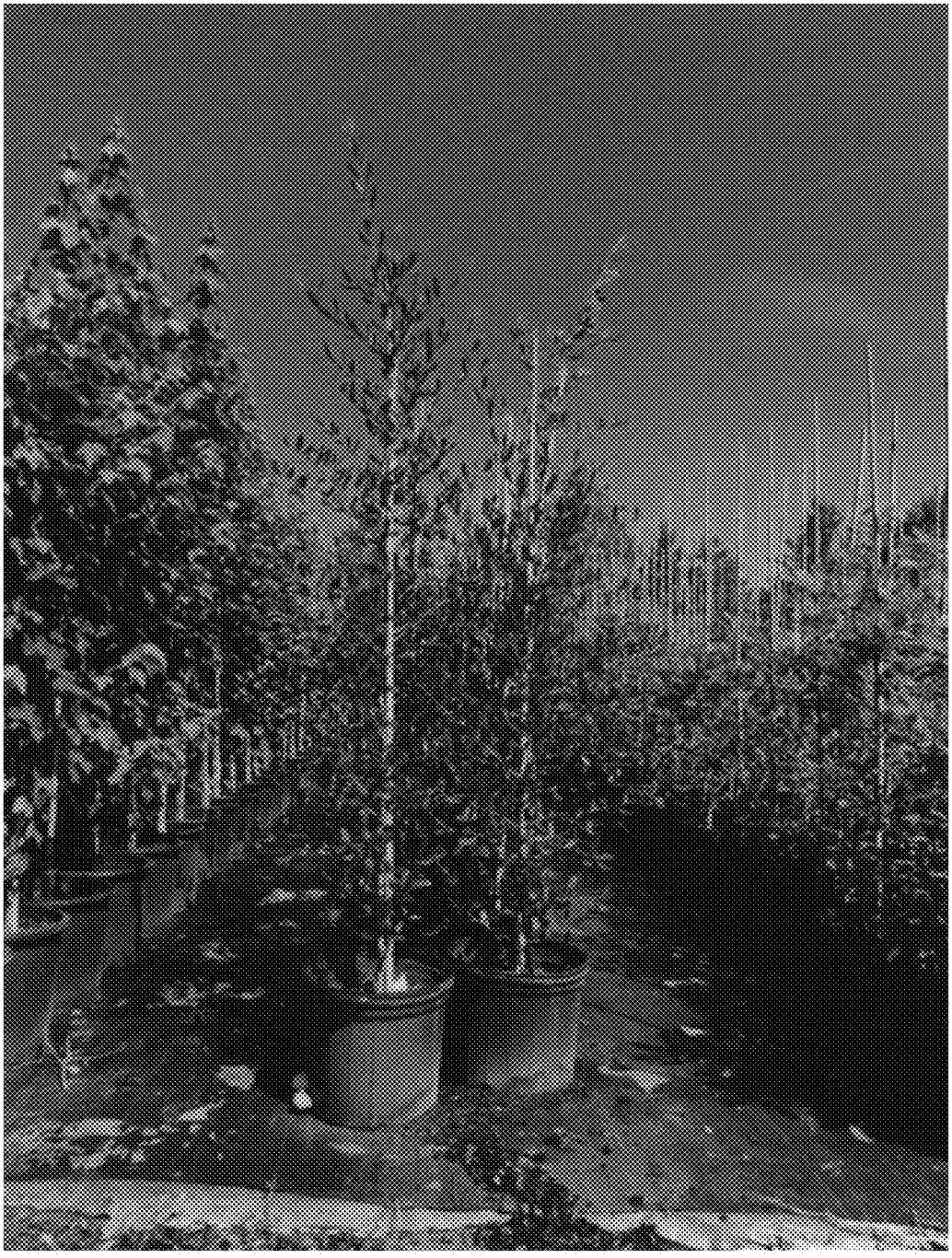

The photograph in FIG. 3 was taken of plants about 14 months in age as grown outdoors in 3-gallon containers in Rutledge, Ga. and provides a view of the plant habit of 'QVCCN' when grown in a container.

The colors in the photographs may differ slightly from the color values cited in the detailed botanical description, which accurately describe the colors of the new *Quercus.*

DETAILED BOTANICAL DESCRIPTION

The following is a detailed description 14-month-old plants of the new cultivar grown outdoors in 3-gallon containers in Rutledge, Ga. with other data collected from the plant about 13 years in age as grown in the ground in Iva, S.C. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period.*—Late March to mid-April depending on weather conditions in the upstate region of South Carolina.

*Plant type.*—Deciduous tree with older leaves retained until new growth appears, (retention is dependent on air temperatures) for an evergreen appearance when retained.

*Plant habit.*—Upright oval with a dense canopy.

*Height and spread.*—Reaches an average of 7 m in height and 5 m in spread as a 13-year-old tree in the landscape.

*Hardiness.*—At least in U.S.D.A Zones 7 to 10.

*Diseases and pests.*—No susceptibility or resistance to diseases or pests has been observed.

*Root description.*—Fibrous, freely branched and 165C in color.

*Propagation.*—Semi-hardwood stem cuttings.

*Root development.*—Cuttings root in about 35 days, about 9 months to produce a young plant from a rooted cutting.

*Growth rate.*—Moderate.

Branch description:

*Branch angles.*—Upper canopy branches more ascending, emerging at a 40° angle from main trunk, lower canopy averages 70° from trunk.

*Branch strength.*—Very strong.

*Branch size* (*as a* 13-*year-old tree*).—Trunk; caliper 28 cm in diameter, 30 cm in height from the soil level, lateral branches; an average of 2.4 m in length and 2 to 9.5 cm in diameter.

*Branch surface.*—Young; slightly pubescent, mature; glabrous and matte, older bark; slightly furrowed and rugose, covered with lenticels 199D in color, 0.5 mm in length.

*Branch color.*—Young emerging stems; 178B turning 197B, Trunk; mottled, 197B and N200B.

*Internode length.*—Average of 3.8 cm.

Foliage description:

*Leaf shape.*—Elliptic to obovate.

*Leaf division.*—Simple.

*Leaf base.*—Round to subcordate to broadly cureate.

*Leaf apex.*—Acute.

*Leaf fragrance.*—None.

*Leaf venation.*—Pinnate, upper surface mid vein 147B, lower surface mid vein 145A, all other veins match leaf color.

*Leaf margins.*—Not lobed, entire.

*Leaf arrangement.*—Alternate.

*Leaf aspect.*—Held outward on pendant petioles, held in an average angle of 45° from branch.

*Leaf attachment.*—Petiolate.

*Leaf surface.*—Upper surface very glossy and leathery, lower surface matte and pubescent.

*Leaf size.*—Average of 6.5 cm in length, 3 cm in width.

*Leaf color.*—Young upper surface 145A, young lower surface N144C, mature upper surface 147A, mature lower surface 147B.

*Petioles.*—Average of 6.3 mm in length, 1 mm in width, held at a 45° angle, smooth and glabrous surface surface, 197B in color.

Flower description:

*Inflorescence type.*—Typical of the species, lasting abut 2 weeks, male catkins and small female flowers in axils of leaves consisting of 3-stigmatic styles over a cup-like ovary, plants in bloom were unavailable for a detailed description.

*Fruit/seeds.*—Acorns; oval to ovate in shape, apex is short, acute with an ellipsoidal cap, 2 cm in length, 1.5 cm in width, cap is 1.75 cm in length and 1.5 cm in width, 11C in color at apex and 144A in color on portion not covered with cap, cap is 161A in color with nodules 199D in color.

It is claimed:

1. A new and distinct cultivar of *Quercus* tree named 'QVCCN' as herein illustrated and described.

* * * * *